(12) United States Patent
Robinson et al.

(10) Patent No.: US 6,982,429 B2
(45) Date of Patent: Jan. 3, 2006

(54) TRANSMISSION ELECTRON MICROSCOPE SAMPLE PREPARATION

(76) Inventors: Joseph Robinson, 2056 NW. Aloclak Dr. Suite 323, Hillsboro, OR (US) 97124; Kenneth H. Church, 5202-2 N. Richmond Hill Rd., Stillwater, OK (US) 74075

( * ) Notice: Subject to any disclaimer, the term of this patent is extended or adjusted under 35 U.S.C. 154(b) by 0 days.

(21) Appl. No.: 10/886,201

(22) Filed: Jul. 6, 2004

(65) Prior Publication Data

US 2004/0245466 A1    Dec. 9, 2004

Related U.S. Application Data

(63) Continuation of application No. 09/920,715, filed on Aug. 3, 2001, now Pat. No. 6,841,788.

(60) Provisional application No. 60/222,728, filed on Aug. 3, 2000.

(51) Int. Cl.
  *H01J 37/31*    (2006.01)
  *B23K 26/38*    (2006.01)
(52) U.S. Cl. .............................. 250/492.3; 219/121.68
(58) Field of Classification Search .......... 219/121.68, 219/121.69, 121.82; 250/492.3, 311
  See application file for complete search history.

(56) References Cited

U.S. PATENT DOCUMENTS

| | | | | |
|---|---|---|---|---|
| 5,059,764 A | * | 10/1991 | Baer | 219/121.68 |
| 5,208,437 A | * | 5/1993 | Miyauchi et al. | 219/121.67 |
| 5,350,921 A | * | 9/1994 | Aoyama et al. | 250/311 |
| 5,656,186 A | * | 8/1997 | Mourou et al. | 219/121.69 |
| 5,922,224 A | * | 7/1999 | Broekroelofs | 219/121.72 |
| 6,140,603 A | * | 10/2000 | Hwang et al. | 219/121.69 |
| 6,300,631 B1 | * | 10/2001 | Shofner | 250/311 |
| 6,489,589 B1 | * | 12/2002 | Alexander | 219/121.69 |
| 6,841,788 B1 | * | 1/2005 | Robinson et al. | 250/492.3 |
| 2004/0016888 A1 | * | 1/2004 | Haraguchi | 250/440.11 |

FOREIGN PATENT DOCUMENTS

| | | | |
|---|---|---|---|
| JP | 9-96595 A | * | 4/1997 |
| JP | 11-145087 A | * | 5/1999 |
| JP | 11-160210 A | * | 6/1999 |
| JP | 2000-329663 A | * | 11/2000 |

* cited by examiner

*Primary Examiner*—Geoffrey S. Evans
(74) *Attorney, Agent, or Firm*—Kolisch Hartwell, P.C.

(57) ABSTRACT

Sample preparation apparatus and method includes a wafer stage platform with an optical microscope and integrated pattern recognition to automatically address specific locations on the wafer sample of interest. A laser attaches to the optical microscope to mill a set pattern around the area of interest. A precision micro-manipulator engages the sample support structure, extracts the structure, and places the structure in a TEM holder or holder tip. The holder or holder tip can then be placed inside a FIB for final thinning, followed by direct transfer into the TEM.

9 Claims, 2 Drawing Sheets

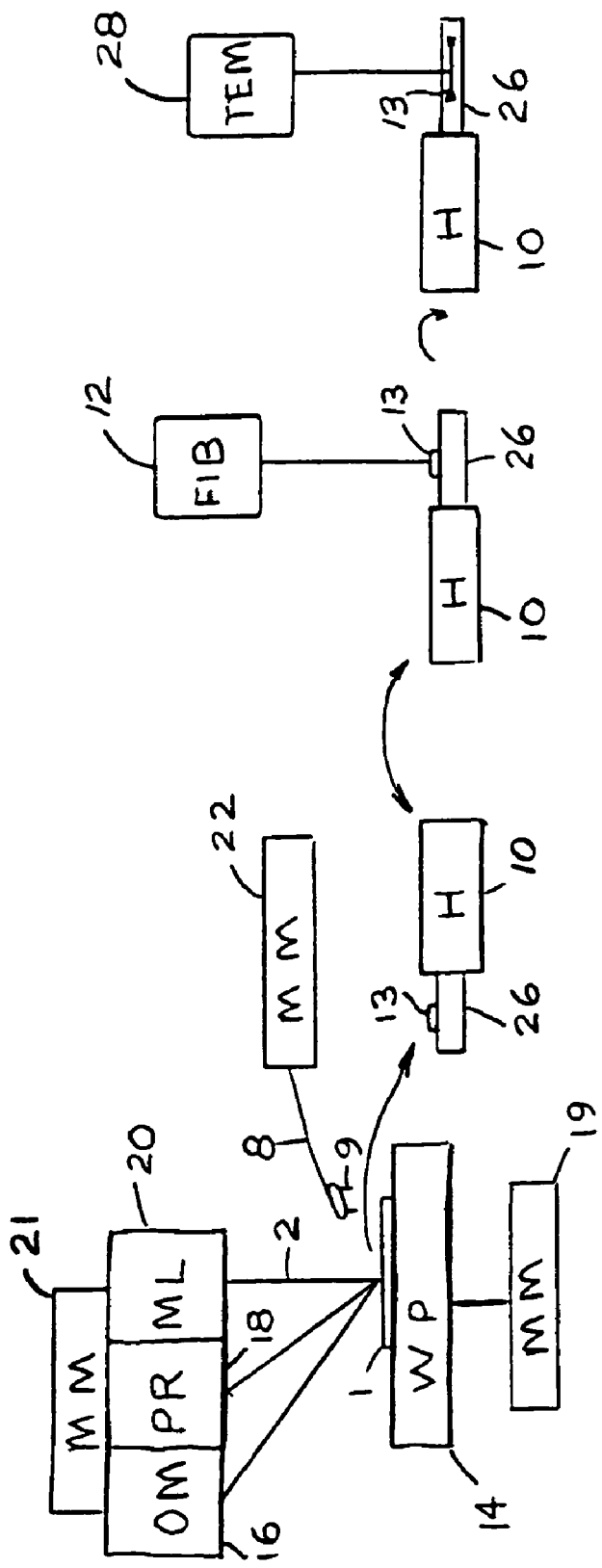

TRANSMISSION ELECTRON MICROSCOPE SAMPLE PREPARATION

CROSS-REFERENCE TO RELATED APPLICATION

This is a continuation of U.S. patent application Ser. No. 09/920,715 filed Aug. 3, 2001, now U.S. Pat. No. 6,841,788.

This application claims the benefit of U.S. Provisional Application No. 60/222,728 filed Aug. 3, 2000.

BACKGROUND OF THE INVENTION

Transmission electron microscopes (TEMs) have been used in a variety of scientific disciplines for 50 years. A TEM works in a way fundamentally similar to a light microscope except for the use of an electron beam instead of light. Electrons have a much shorter wavelength and consequently allow viewers to see features approaching atomic size (<1 nanometer) in comparison to a limit of 100 nm (0.1 $\mu$m for light).

Over the last 50 years, transmission electron microscopy (TEM) technology and its applications have undergone tremendous advances. TEM has become an important analytical tool in many disciplines that require visualization and/or imaging of features less than one nanometer in size, a resolution at least two orders of magnitude greater than that available to optical microscopy.

Unfortunately, the preparation of samples for TEM analysis is fraught with difficulties. TEM only works with samples made thin enough to be transparent to electrons, a distance on the order of 50 nm. Thinning samples through cutting or grinding is especially difficult for hard, tough, and especially brittle materials; furthermore, attempts to meet even reasonable standards of reproducibility and throughput often fail. The bottom line is that successful TEM sample preparation generally requires the use of highly trained, reliable, experienced, and hence very expensive technical personnel.

There are many practical difficulties inherent to using a transmission electron microscope (TEM) to image microstructures. Samples must first be thinned to an ultra-thin membrane transparent to electrons: approximately 50 nm (0.00005 mm) or less. This is less than 1/1000 of the diameter of a human hair. In reality, this is extremely difficult to accomplish on hard materials since many crystalline materials, such as silicon, do not lend themselves to conventional cutting or grinding techniques. Additionally, one cannot easily observe the area of interest while thinning it, and handling the minuscule samples requires a highly trained, dexterous technician.

In the past ten years, the market for TEMs has been static at about 250 units per year (100 in the U.S.). As Government funding decreased for life sciences in general, demand for biological TEMs declined. Offsetting this trend, high-end analytical TEMs for materials (metals, ceramics, semiconductors, superconductors, etc.) increased, largely due to the need to view crystalline structures and thin film interfaces at the highest possible visual acuity. The demand for TEM images continues to grow precipitously in the semiconductor market segment as companies move to smaller design rules and deeper vertical integration.

The increasing demand for TEM does not necessarily translate directly into instrument sales, since the real bottleneck in productivity continues to be the tedious and time-consuming nature of sample preparation. Several labs have commented that their TEMs sit idle much of the time, waiting for quality samples of the right area to be prepared.

There are significant differences in requirements between customers who extract samples from full wafers vs. customers who analyze samples from bulk materials. The bulk sample customers represent a wide cross-section of analytical electron microscope users in a broad range of materials applications in institutional and industrial settings. Although in the majority, they do not have the same critical need for productivity that semiconductor customers have. The wafer customers, best represented by process development and yield engineers, have the following general requirements: 1) they want cross sections of specific devices or defects extracted directly from wafers; 2) they want specific location coordinates transferred from other equipment; 3) they want sample preparation, from full wafer to imaging, to be as fast as possible; 4) they want confidence that an exact location on a wafer can be sampled; 5) they want a minimum of artifact formation; 6) they want the process automated to the fullest possible extent; and 7) they do not want to sacrifice the entire wafer for a single sample preparation.

Within the current general approach of TEM sample preparation, there are subtle variations; however, each consists of a technique for removing a bulk sample from the wafer, reducing the area of interest to an ultra-thin membrane, and finally transferring the membrane to the TEM. The current approaches to TEM sample preparation include using high precision diamond saws, broad beam thinning techniques and single beam focused ion beam (FIB) milling methods. In most these approaches, the sample must be manually transferred to the TEM for analysis.

High precision diamond saws are currently available for TEM sample preparation. Each claims to be able to reach the right spot on a wafer automatically and create an approximate 1 $\mu$m×1 $\mu$m block containing the sample. The process takes anywhere from 30 minutes to two hours, depending upon the skill of the technician. Clearly, the major drawback to this type of apparatus is the fact that the wafer is sacrificed, and only one sample per wafer is utilized.

The broad beam thinning technique of TEM sample preparation is virtually obsolete for full wafer sample extraction simply because it is slow, the area of interest cannot be targeted, and the ultimate thickness is variable.

There are two different single beam FIB approaches for TEM sample preparation. In one approach, multiple samples can be automatically processed up to, but not including the final cut. After thinning, samples must then be manually transferred to a support grid and into a TEM holder. Some commercial TEM sample preparation methods offer a detachable tip "FIB-EM" that can be pre-mounted on the FIB stage before thinning in an attempt to reduce transfer damage.

A second approach for single beam FIB sample preparation allows users to insert a TEM sample rod into an FIB through an airlock, thus avoiding manual handling of the delicate thin section any time after it is milled. This reduces the chance of physical damage.

The use of a dual beam (combination FIB and SEM) for sample thinning and extraction has become the dominant technique for wafer applications. The area of interest of the wafer can be located using navigation software, and ultra-thin sections can then be cut directly from the wafer. This technique completely avoids the intermediary diamond saw and lapping steps. Unfortunately, the ultra-thin membrane itself must be lifted from the wafer and transferred to a grid manually in this approach.

There are three methods available for transferring the membrane from wafer to TEM sample holder. All three permit the user to prepare multiple samples from one wafer without destroying the rest of the devices on the wafer. One approach allows for picking up thin sections of TEM samples by electrostatic attraction. In this method, FIB prepared samples are manually located under a binocular microscope. The membrane is then touched with a charged micro-manipulator probe in the hope that static attraction between the thin membrane and the probe will occur. Even with an expert technician at the controls, membranes are likely to disappear or crumble during the manual transfer.

A second technique involves grabbing the membrane inside the dual beam with a micro-tweezer. If the membrane survives the detachment from the substrate and tweezer jaws, the operator must then gingerly place the membrane on a TEM grid. The TEM grid must then be transferred to the TEM sample holder. Although there is better visual observation possible at the extraction site, there is also significant increased physical handling.

The newest technique was developed by Tom Moore, and is called the Moore Technique. In that approach, a probe is actually welded to the finished membrane inside the FIB using the FIB's metal deposition capability. The FIB then cuts the membrane free from the matrix. It can then be transferred to a grid, where the probe weld is cut, and the membrane can then be welded to the grid.

Needs exist for a TEM sample preparation that is simple, cost effective, and automated to decrease the risk of human error when transferring samples to a TEM for analysis.

SUMMARY OF THE INVENTION

In earlier years, TEM sample preparation often required more than a day. Recently, the application (principally by the semiconductor industry) of focused ion beam (FIB) milling technology to TEM sample preparation has shortened that time to about three hours. With the approach of the present invention, TEM sample preparation time is cut from about 30 minutes to about two hours, or between a 16% to 67% reduction in preparation time.

Currently, TEM sample preparation for semiconductor devices is typically done with diamond saws, microtweezers, and finished with a focused ion beam (FIB) milling.

This invention replaces the diamond saw and cut or machine with a laser. Typical laser machining leaves thermal damage on the micrometer scale. Since the device size scale is micrometers and less, thermal damage is unacceptable. To eliminate thermal damage caused by laser ablation, a femtosecond (one quadrillionth or $10^{-15}$ second) laser is used in the present invention.

Femto-laser machining is not well known; however, it has been done on various materials for a couple of years. The present invention is a tool with femto-laser machining capability. The laser cuts a sample out of a wafer that is strategically placed to handle the cut piece. The cut piece is on the order of 5 $\mu$m by 10 $\mu$m by the thickness of the wafer, 750 $\mu$m. The piece must be turned on its edge and trimmed back. The final polishing or thinning may be done with an FIB milling. The laser cutting or milling leaves a thin layer between two large ends at the top of a large supporting blade of the test material. The block is turned on its side so that the thin layer may be examined by a TEM.

The advantage of the laser milling technology of the present invention over the present state of the art is that it does not require the removal of a fragile membrane from a silicon wafer, which is the case with current FIB TEM sample preparation. Rather, a laser removes a shaped block from the wafer which contains an area thinned for TEM and guide holes for mounting to a bracket designed to fit both FIB and TEM instruments.

The laser-milling instrument of the present invention consists of a wafer stage platform connected to an optical microscope and a computer-operated integrated-pattern-recognition assembly, a milling laser, and a precision micro-manipulator.

The laser-milling instrument of the present invention as a whole represents an innovation, with the newest portion including the laser itself. The phenomenon of laser ablation of silicon has been studied for years, but the results with older nanosecond-regime (NR) laser technologies would not suffice for the small structures of current and near-future silicon integrated-circuit technologies. Lasers operating in the sub-picosecond regime (SPR) are relatively new inventions, and have only been applied to the ablation of silicon since about 1995. These lasers offer the promise of superior performance, and ease of application to milling.

The present invention is a new technique having a number of advantages over the current commercially available solutions. Instead of trying to extract a fragile, minuscule membrane from a wafer after FIB processing, a laser is used to cut out a uniform sample shaped block containing the thinned area of interest and a pair of laser drilled holes. The holes are mated to twin probes mounted on a bracket that can be fitted directly to a FIB stage or modified TEM holder. The membrane is protected by the bracket throughout the preparation and transfer steps of the process. Because the sample has been pre-cut with a precision laser, there is a minimum of actual trimming required in the FIB, eliminating 45 minutes to two hours of milling time.

The essential difference between this and all other currently available techniques is that the surrounding silicon substrate of the wafer is used as part of the support strategy for protecting the FIB prepared thin membrane.

A preferred embodiment has a wafer stage platform with an optical microscope and integrated pattern recognition to automatically address specific locations on the wafer. Preferably, a laser attaches to the optical microscope to mill a set pattern around the area of interest. Finally, there is a precision micro-manipulator that engages the sample support structure, extracts the structure, and places the structure in a TEM holder or holder tip.

The process of the present invention provides a safe, easy to use, semi-automated, and efficient method for cutting and extracting a specific nano-level feature from a wafer. The method allows a user to remove most of the material in situ, while also providing protection for subsequent steps. The holder or holder tip can then be placed inside a FIB for final thinning, followed by direct transfer into the TEM.

The TEM sample preparation of the present invention results in lower costs per sample. A comparison of the costs involved with TEM sample preparation using the present invention versus using other currently available methods is summarized in Table 1.

These and further and other objects and features of the invention are apparent in the disclosure, which includes the above and ongoing written specification, with the claims and the drawings.

BRIEF DESCRIPTION OF THE DRAWINGS

FIG. 1 is a block diagram of a preferred embodiment of the TEM sample preparation apparatus of the present invention.

DETAILED DESCRIPTION OF THE PREFERRED EMBODIMENTS

Figure 4:
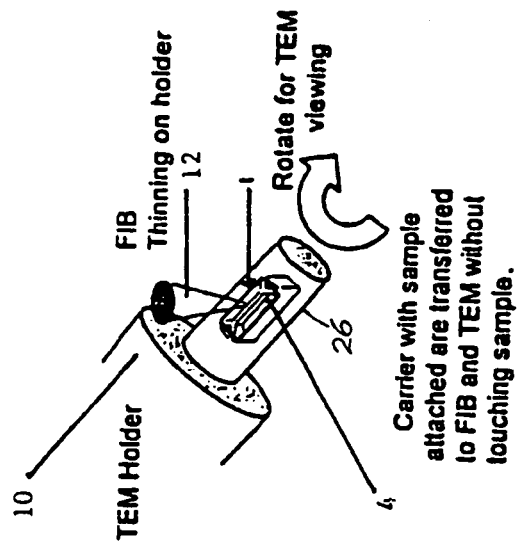
FIG. 4 is a perspective view of a cut wafer on a TEM Holder for manipulation by an FIB.

The process of the present invention provides a safe, easy to use, semi-automated, and efficient method for cutting and extracting a specific nano-level feature from a wafer. The method allows a user to remove most of the material in situ, while also providing protection for subsequent steps. The holder or holder tip can then be placed inside a FIB for final thinning, followed by direct transfer into the TEM.

As shown in FIG. 1, a preferred embodiment of the TEM sample preparation apparatus of the present invention has a wafer stage platform 14 and an optical microscope 16. A computer operated pattern recognition assembly 18 is connected to the optical microscope for automatically addressing specific locations of areas of interest 4 on the wafer 1 as selected by the optical microscope. Preferably, a milling laser 20 is attached to the optical microscope 16 to mill a set pattern around an area of interest 4 of the wafer 1. The pattern includes forming a thin sample strip 15 with ends 5 and holes 6, followed by cutting the block 13 from the wafer.

The phenomenon of laser ablation of silicon has been studied for years, but the results with older nanosecond-regime (NR) laser technologies operating at one billionth of $10^{-9}$ seconds would not have sufficed for the small structures of current and near-future silicon integrated-circuit technologies. Lasers operating in the sub-picosecond regime (SPR) are relatively new inventions, and have only been applied to the ablation of silicon since about 1995. These lasers offer the promise of superior performance, and ease of application to milling.

Table 1 shows an overview and comparison of TEM sample preparation procedures including that of the present invention.

The milling laser 20 is preferably a femto-laser. Typical laser machining leaves thermal damage on the micrometer scale. Since the device size scale is micrometers and less, thermal damage is unacceptable. To eliminate thermal damage caused by laser ablation, a femtosecond laser 20 is used in the present invention. Using a femto-laser as the milling laser 20 minimizes thermal damage caused by laser ablation.

A micro-manipulator 21 moves the milling laser 20 to form the sample strip 15 and cut the block 13 from the wafer 1. Alternatively, a micro-manipulator 19 moves the wafer platform during laser milling and cutting.

A precision micro-manipulator 22 moves an arm 8 with dual stylus 9 to engage the sample support structure ends for extracting the cut block 13 from the wafer 1 and places block 13 in a TEM holder tip 26 of a TEM holder 10. The sample strip is then finished and thinned by an FIB 12. The cut wafer block 13 is then rotated 90° by the TEM holder 10 and is transferred to a TEM 28 for analysis.

Figure 3:
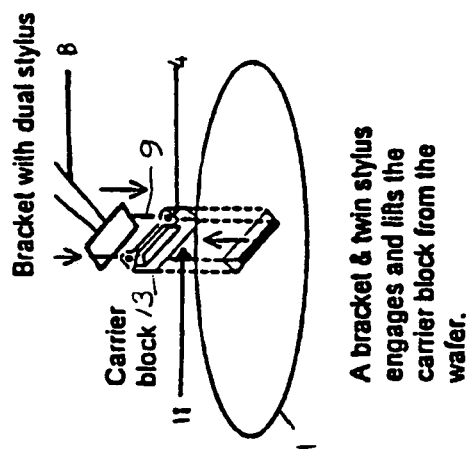
FIG. 3 is a perspective view of a bracket with dual stylus lifting a carrier block from a wafer.
Figure 2:
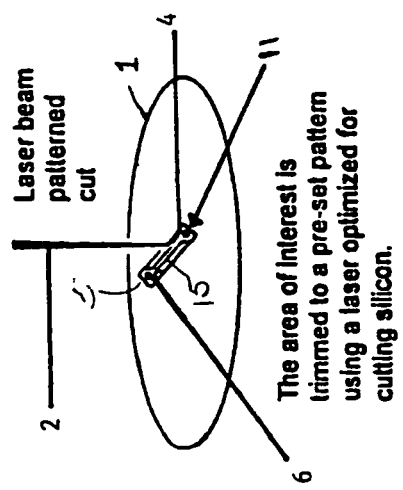
FIG. 2 is a perspective view of a laser beam cutting and drilling an area of interest from a wafer.

As shown in FIGS. 2, 3, and 4, the area of interest 4 is trimmed to a pre-set pattern 11 using a laser optimized for cutting silicon from the wafer 1 creating thin sample 15. A bracket 8 with twin stylus 9 engages and lifts the carrier block 13 from the wafer 1. The carrier block 13 with sample 15 attached are transferred on holder 10 for FIB 12 thinning and TEM inspection without touching sample 15. Holder 10 is then rotated for TEM viewing of the sample 15.

To prepare a TEM sample 15, the milling laser 20 cuts the sample out of a wafer 1 using a laser beam 2, as shown in FIG. 2. The wafer 1 is strategically placed to withstand the cutting. The cut block 13 preferably is approximately 5 $\mu$m by 10 $\mu$m the thickness of the wafer 1, which is 750 $\mu$m. The cut area of interest 4 must be turned on its edge for inspection. It may be trimmed first and subjected to final polishing or thinning with an FIB 12.

The advantage of the laser milling technology of the present invention is that it does not require the removal of a fragile membrane from a silicon wafer 1, which is the case with current FIB TEM sample preparation. Rather, the cutting and milling laser 2 removes a shaped block 13 from the wafer 1.

The shaped block contains a sample strip 15 in a selected area 4 thinned for TEM inspection. Ends 5 with laser-drilled guide holes 6 for picking up by an arm or bracket 8 with dual stylus 9, as shown in FIG. 3, is designed to fit both FIB 12 and TEM 28 instruments. In this way, the TEM sample preparation of the current invention uses the silicon substrate of the wafer block 13 to protect the thin membrane sample 15 taken from the area of interest 4 in the wafer 1.

As shown in FIG. 4, once a wafer 1 has been cut and lifted by the bracket 8 with dual stylus 9, which is controlled by micro-manipulator 22. The cut wafer block 13 is transferred to a TEM holder 10 or a TEM holder tip 26. The cut wafer block 13 is then subject to manipulation by an FIB 12 to prepare the sample for analysis by a TEM 28.

With the present invention, TEM sample preparation time is cut from about 45 minutes to about two hours, up to a 67% reduction in preparation time.

While the invention has been described with reference to specific embodiments, modifications and variations of the invention may be constructed without departing from the scope of the invention, which is defined in the following claims.

We claim:

1. A sample preparation apparatus, comprising a support, a microscope, a pattern recognition assembly and a femtosecond milling laser coupled to the support, and a sample of interest;

wherein the microscope is an optical microscope, the femtosecond laser is configured for milling a desired pattern on a portion of interest of the sample, and further comprising a sample holder for the microscope, and a precision micro-manipulator engaging the support for extracting and positioning the portion of interest on the sample holder.

2. The apparatus of claim 1, wherein the pattern recognition assembly is a computer-operated integrated pattern recognition for automatically addressing specific locations on the sample.

3. The apparatus of claim 1, wherein the sample is silicon wafer.

4. The apparatus of claim 1, wherein the sample comprises a substrate forming a membrane support for protecting the portion of interest after it is extracted from the sample by laser ablation.

5. The apparatus of claim 4, further comprising a focused ion beam source for thinning the sample, and a transmission electron microscope for analyzing the sample, and a bracket configured for use with both the transmission electron microscope and the focused ion beam source.

6. The apparatus of claim 5, wherein the portion of interest is a shaped block comprising an area thinned for the transmission electron microscope and guide holes on the block for mounting to the bracket.

7. The apparatus of claim 6, wherein the area is a thin layer between two large ends of the block having a supporting blade on a top side.

8. The apparatus of claim 6, further comprising probes mounted on the bracket for mating with the holes on the block and for holding the block on its side on the bracket, and twin stylus on the bracket for engaging and lifting the block from the sample, transferring to the sample holder for thinning with the focused ion beam source and transferring to the transmission electron microscope for inspection and analysis without contamination of the block.

9. The apparatus of claim 1, wherein the desired pattern has at least one feature having a dimension on the order of micrometers or less.

* * * * *